US00PP08149P

United States Patent [19]

van der Knapp

[11] Patent Number: Plant 8,149

[45] Date of Patent: Feb. 16, 1993

[54] CHRYSANTHEMUM PLANT — JANNEL CULTIVAR

[75] Inventor: Jacques C. M. van der Knapp, De Lier, Netherlands

[73] Assignee: Fides Beheer B.V., De Lier, Netherlands

[21] Appl. No.: 721,391

[22] Filed: Jun. 26, 1991

[51] Int. Cl.[5] ..... A01H 5/00

[52] U.S. Cl. ..... Plt./77

[58] Field of Search ..... Plt./77

*Primary Examiner*—Howard J. Locker

*Attorney, Agent, or Firm*—Burns, Doane, Swecker & Mathis

[57] ABSTRACT

A new and distinct cultivar of Chrysanthemum plant named Jannel is provided. The new cultivar was the result of a controlled breeding program wherein the Green Peas cultivar (U.S. Plant Pat. No. 6,735) was pollinated by the Keystone cultivar (U.S. Plant Pat. No. 5,946). More specifically, the new cultivar forms attractive cream white flowers of the pompon type which have a green center (as illustrated). The inflorescence tends to be pyramidal in configuration. The response period of the flowers is approximately nine weeks. Reduced susceptibility to leaf miner is exhibited. The new cultivar is particularly suited for use in the production of a cut decorative spray under greenhouse conditions.

1 Drawing Sheet

SUMMARY OF THE INVENTION

The present invention comprises a new and distinct cultivar of Chrysanthemum, botanically known as *Chrysanthemum morifolium*, Ramat., and hereinafter is referred to by the cultivar name Jannel.

The new cultivar is the product of a planned breeding program which had as its objective the creation of a new Chrysanthemum cultivar which exhibits attractive flowers of the pompon type having white ray florets and a green flower center, a flower response period of approximately nine weeks, and the ability to produce flowers of commercially acceptable quality throughout the year in a cut mum production program. Such combination of traits is not believed to have been present in the previously available Chrysanthemum cultivars. This objective was satisfactorily fulfilled in the cultivar of the present invention.

The breeding program which resulted in the production of the new cultivar of the present invention was carried out in a controlled environment during 1985 at De Lier, The Netherlands. The female parent (i.e., the seed parent) was the Green Peas cultivar (U.S. Plant Pat. No. 6,735) and the male parent (i.e., the pollen parent) was the Keystone cultivar (U.S. Plant Pat. No. 5,946). The parentage of the new cultivar can be summarized as follows:

GREEN PEAS×KEYSTONE.

The seeds resulting from the above pollination were sown and plantlets were obtained which were physically and biologically different from each other. Selective study during 1986 resulted in the identification of a single plant of the new cultivar.

It was found that the new cultivar of the present invention:

(a) exhibits decorative flowers having an overall diameter of approximately 60 to 70 mm. wherein the ray florets are cream white and the flower center is light green, (b) bears flowers in a somewhat pyramidal configuration, (c) exhibits a flower response period of approximately nine weeks, (d) exhibits a reduced susceptibility to leaf miner, (e) forms attractive dark green foliage, and (f) has the ability to produce flowers of commercially acceptable quality throughout the year in a cut mum production program.

Asexual reproduction of the new cultivar by cuttings initially taken during 1986, as performed at De Lier, The Netherlands, in a controlled environment has demonstrated that the characteristics of the new cultivar as herein disclosed are firmly fixed and are retained through successive generations of asexual propagation.

Jannel has not been observed under all possible environmental conditions to date. Accordingly, it is possible that the phenotype may vary somewhat with variations in the environment, such as temperature, light, day length, contact with pesticides and/or subjection to growth retardant treatments.

When the new cultivar of the present invention is compared to the Green Peas cultivar, the Jannel cultivar is found to exhibit slightly less vegetative growth (e.g., assumes a height of approximately 90 cm. vs. approximately 110 cm.), exhibits a slower flower response period (e.g., approximately nine weeks vs. approximately eight weeks), exhibits less of a pompon flower type, exhibits a more decorative appearance, and exhibits more tolerance to leaf miner. The cream white ray floret coloration, the light green flower center, and the tolerance to low and high temperatures are substantially identical to the corresponding characteristics of the Green Peas cultivar.

BRIEF DESCRIPTION OF THE PHOTOGRAPH

The accompanying photograph shows as nearly true as it is reasonably possible to make the same in a color illustration of this character, a typical specimen of an overall plant of the new cultivar. The plant was grown in a greenhouse at De Lier, The Netherlands.

DETAILED DESCRIPTION

The chart used in the identification of colors described hereafter is the R.H.S. Colour Chart of The Royal Horticultural Society, London, England. The color values were determined at 11:00 a.m. to 12:00 noon under natural daylight conditions at De Lier, The Netherlands, on May 15, 1991. The plants described were grown under standard greenhouse conditions which approximate those commonly utilized for the production of cut mums.

Classification:

*Botanical.*—*Chrysanthemum morifolium* Ramat., cv. Jannel.

*Commercial.*—Cut decorative spray.

INFLORESCENCE

A. Capitulum:

*Form.*—Pyramidal.

*Type.*—Decorative.

*Diameter across face.*—Approximately 60 to 70 mm. on average.

B. Corolla of ray and disc florets:

*Color (general tonality from a distance of three meters).*—White with green center.

*Color ray florets.*—(top surface) — Cream white, White Group 155B. (lower surface) — Cream white, White group 155B.

*Color disc florets.*—Light green, Green Group 138B.

C. Reproductive organs:

*Androecium.*—Not present.

*Gynoecium.*—Present in ray florets.

PLANT

A. General appearance:

*Height.*—Approximately 90 cm. on average.

B. Foliage:

*Color (upper surface).*—Yellow-Green Group 147A.

*Color (under surface).*—Yellow-Green Group 147B.

I claim:

1. A new and distinct cultivar of Chrysanthemum plant named Jannel, substantially as herein shown and described, which:

(a) exhibits decorative flowers having an overall diameter of approximately 60 to 70 mm. wherein the ray florets are cream white and the flower center is light green, (b) bears flowers in a somewhat pyramidal configuration, (c) exhibits a flower response period of approximately nine weeks, (d) exhibits a reduced susceptibility to leaf miner, (e) forms attractive dark green foliage, and (f) has the ability to produce flowers of commercially acceptable quality throughout the year in a cut mum production program.

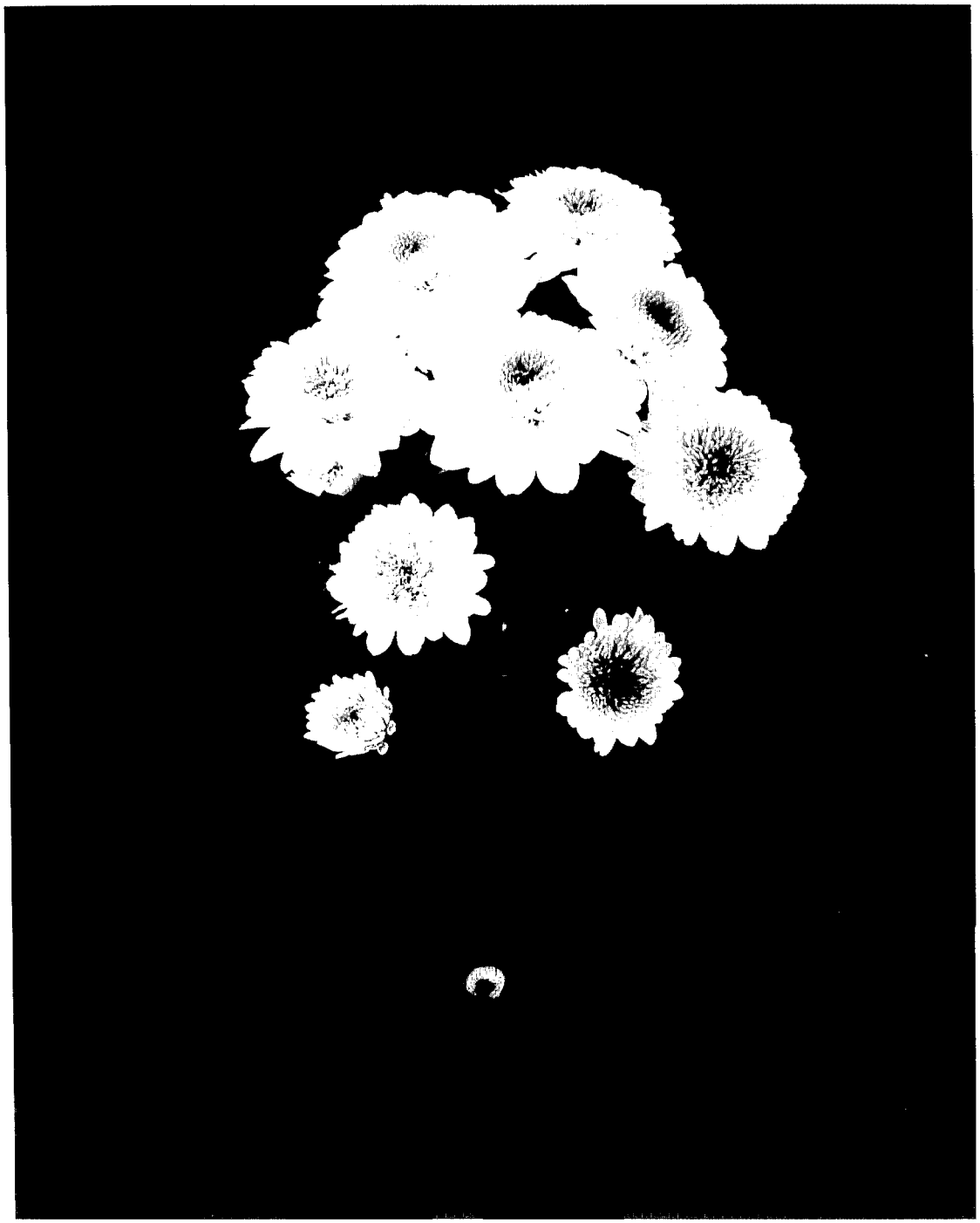

* * * * *